(12) United States Patent
Jeong

(10) Patent No.: US 9,566,228 B2
(45) Date of Patent: Feb. 14, 2017

(54) BUBBLE TYPE WATERLESS SHAMPOO COMPOSITION

(71) Applicant: Seok Hoon Jeong, Anyang-si (KR)

(72) Inventor: Seok Hoon Jeong, Anyang-si (KR)

( * ) Notice: Subject to any disclaimer, the term of this patent is extended or adjusted under 35 U.S.C. 154(b) by 319 days.

(21) Appl. No.: 14/551,482

(22) Filed: Nov. 24, 2014

(65) Prior Publication Data

US 2016/0143833 A1     May 26, 2016

(51) Int. Cl.

| | | |
|---|---|---|
| *A61K 8/64* | (2006.01) | |
| *A61K 8/65* | (2006.01) | |
| *A61Q 5/02* | (2006.01) | |
| *A61K 8/365* | (2006.01) | |
| *A61K 8/19* | (2006.01) | |
| *A61K 8/92* | (2006.01) | |
| *A61K 8/368* | (2006.01) | |
| *A61K 8/34* | (2006.01) | |
| *A61K 8/44* | (2006.01) | |
| *A61K 8/04* | (2006.01) | |

(52) U.S. Cl.
CPC ............... *A61K 8/65* (2013.01); *A61K 8/046* (2013.01); *A61K 8/19* (2013.01); *A61K 8/345* (2013.01); *A61K 8/365* (2013.01); *A61K 8/368* (2013.01); *A61K 8/442* (2013.01); *A61K 8/64* (2013.01); *A61K 8/922* (2013.01); *A61Q 5/02* (2013.01); *A61K 2800/522* (2013.01)

(58) Field of Classification Search
None
See application file for complete search history.

(56) References Cited

U.S. PATENT DOCUMENTS

2002/0054861 A1\*    5/2002   Schmucker ............ A61K 8/442
                                                                                        424/70.1

\* cited by examiner

*Primary Examiner* — Nannette Holloman
(74) *Attorney, Agent, or Firm* — Im IP Law; C. Andrew Im

(57) ABSTRACT

A bubble type waterless shampoo composition. 0.1 to 5 wt % of potassium cocoyl hydrolyzed collagen and 0.01 to 2 wt % of palmitoyl oligopeptide as natural surfactants. 0.1 to 7 wt % of cocamidopropyl betaine as an amphoteric ion. 0.01 to 0.8 wt % of a citric acid as an organic acid. 0.1 to 4 wt % of sodium carbonate as inorganic salt. 0.01 to 0.5 wt % of *origanum vulgare* leaf oil. 0.01 to 0.6 wt % of a gallic acid. 0.01 to 3 wt % of glycerin. The rest of aqua water having a function of a solvent made by refining tap water through distilling or ion-exchange resin ion.

4 Claims, 1 Drawing Sheet

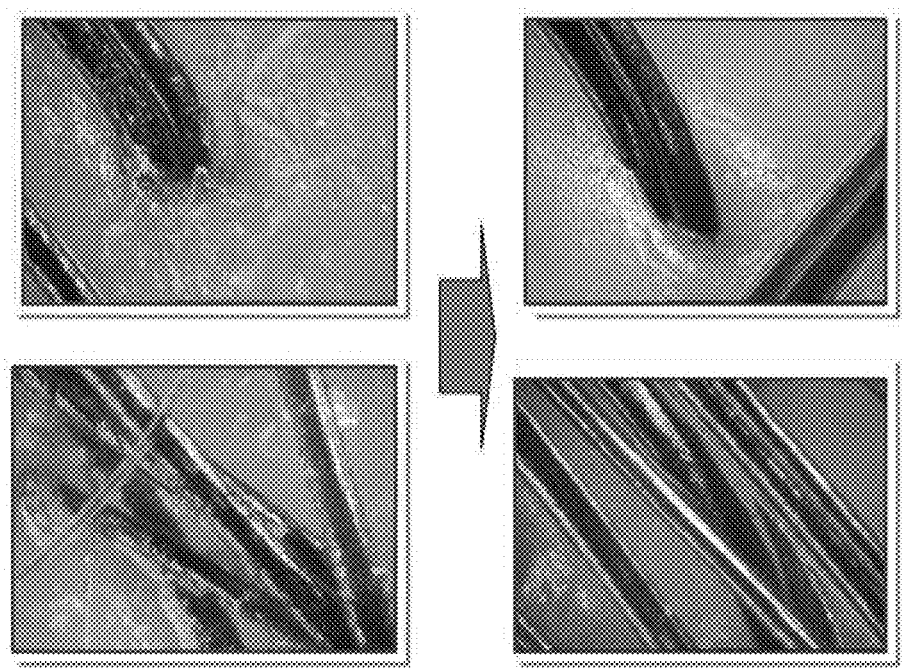

BUBBLE TYPE WATERLESS SHAMPOO COMPOSITION

BACKGROUND OF THE INVENTION

Field of the Invention

The present invention relates to a bubble type waterless shampoo composition that is capable of conducting scalp conditioning and scalp care, without having any water, and more particularly, to a bubble type waterless shampoo composition that is capable of being conveniently used for patients before and after operations, the aged, the disabled, and people during outdoor activities who do not have their scalp care for a long period of time, wherein the bubble type waterless shampoo composition is applicable to a pumping type shampoo, a spray type shampoo, a gel type shampoo and the like.

Background of the Related Art

In an industrial society, people's hair becomes dirty by means of dust generated from various pollution and outside stimulus. The dirty hair is cleaned with a shampoo, and in the modern society where the living levels of the peoples are improved, shampooing is done almost everyday, which undesirably causes the damages on the hair.

Generally, a conventional shampoo composition includes base components such as an anionic surfactant having functions of providing a cleaning force and bubbles, a nonionic surfactant having functions of providing solubilization and emulsifying and dispersing effects, a pH control agent, a thickening agent, a preservative and water, and selective additives such as a conditioning agent, a moisturizing agent, perfume and a pigment. Especially, the conventional shampoo composition includes 40 to 50 wt % of the surfactants and 45 to 55 wt % of water.

The conventional shampoo composition has the shape of a paste phase having high viscosity. Accordingly, the conventional shampoo composition is contained in a pumping container from which the content is discharged through pumping.

So as to clean hair, further, water is first applied to hair, and a shampoo is then applied to the hair to generate bubbles through massaging and cleaned with a large quantity of water. Finally, the water remaining on the hair is removed with a dry towel.

In this case, the sanitary and shiny states of the hair become better, but the conventional shampoo composition includes a large amount of synthetic surfactants giving stimulus to skin and hair, which is very dangerous to those people having sensitive skin and hair to cause their skin and hair to be damaged.

Further, the conventional shampoo composition has a shape of the paste phase having high viscosity. When hair cleaning, water is necessarily applied to hair, and the shampoo is then applied to the hair to generate bubbles through massaging and cleaned with a large quantity of water.

Especially, there are the limitations in time and places when those people such as the aged, long-stay patients and patients on the danger list, the social weak like the disabled, mariners, soldiers, mountain-climbers, travelers in remote places, leisure participants enjoying fishing, camping, cycling, motorcycling and the like, and the people living in the places where water is lacking like a desert area and a cold area clean their hair with the conventional shampoo composition. In more detail, the cleaning processes are very inconveniently conducted, and after the generation of the bubbles, the cleaning is done with a large amount of water, so that the above-mentioned peoples have the limitations in the use of the conventional shampoo composition.

SUMMARY OF THE INVENTION

Accordingly, the present invention has been made in view of the above-mentioned problems occurring in the prior art, and it is an object of the present invention to provide a bubble type waterless shampoo composition that is capable of making bubbles with natural extracts as effective components thereof and directly spraying the bubbles onto a user's scalp or rubbing his or her scalp against the bubbles put into his or her hand to allow his or her scalp to be enough cleaned, thus providing itching releasing and nutrition supplement effects.

It is another object of the present invention to provide a bubble type waterless shampoo composition that is capable of activating stem cells of scalp and minimizing skin stimulus, thus achieving hair loss prevention.

It is yet another object of the present invention to provide a bubble type waterless shampoo composition that is capable of strengthening skin moisturizing, skin regeneration, and skin and hair conditioning functions if provided as an indoor product.

It is still another object of the present invention to provide a bubble type waterless shampoo composition that is capable of providing ultraviolet protection and antioxidant action to protect a user's scalp and hair from strong ultraviolet rays in his or her outdoor activities if provided as an outdoor product.

It is yet still another object of the present invention to provide a bubble type waterless shampoo composition that is capable of containing a menthol component to refresh his or her scalp, to release dandruff and itching, and to maintain his or her scalp in a healthy state if provided as an outdoor product.

It is yet another object of the present invention to provide a bubble type waterless shampoo composition that is capable of containing natural components having strong antioxidant action to minimize the oxidation occurring on a user's scalp or hair in his or her outdoor activities if provided as an outdoor product.

To accomplish the above-mentioned objects, according to the present invention, there is provided a bubble type waterless shampoo composition including: 0.1 to 5 wt % of potassium cocoyl hydrolyzed collagen as a natural surfactant having a function of a detergent; 0.01 to 2 wt % of palmitoyl oligopeptide as a natural surfactant having a function of a detergent; 0.1 to 7 wt % of cocamidopropyl betaine as an amphoteric ion having functions of an anti-static agent, a hair conditioner, a scalp conditioner, a detergent, a foaming agent and a water-soluble thickening agent; 0.01 to 0.8 wt % of a citric acid as an organic acid having a function of a PH control agent; 0.1 to 4 wt % of sodium carbonate as inorganic salt having a function of a PH control agent; 0.01 to 0.5 wt % of *origanum vulgare* leaf oil having functions of perfume, an antioxidant and a skin protector; 0.01 to 0.6 wt % of a gallic acid having a function of an astringent; 0.01 to 3 wt % of glycerin having functions of a denaturizing agent, perfume, a hair conditioner, a skin moisturizer, a skin protector and a viscosity plasticizer; and the rest of aqua water having a function of a solvent made by refining tap water through distilling or ion-exchange resin ion.

According to the present invention, desirably, the bubble type waterless shampoo composition further includes any one or more of 1 to 5 wt % of *pisum sativum* (pea) peptide having a function of providing hair loss prevention through the activation of stem cells of scalp, 3 to 5 wt % of butylenes glycol having functions of providing skin stimulus release and scalp moisturizing, 0.01 to 0.1 wt % of a sigesbeckia orientalis extract as a natural preservative having a function of preventing the deformation of a product, 0.1 to 5 wt % of a sapindus mukurossi fruit extract as a surfactant having a function of increasing the number of bubbles formed and the duration time of the bubbles, 1 to 5 wt % of PEG-120 methyl glucose dioleate as a thickening agent having functions of reducing the stimulus caused by the surfactant, preventing the reduction of the bubbles of the surfactant and performing scalp moisturizing, and 5 to 20 wt % of decyl glucoside as a natural surfactant having a function of biodegradability.

According to the present invention, desirably, the bubble type waterless shampoo composition further includes any one or more of any one or more of 0.01 to 0.2 wt % of saponin having functions of providing an antioxidant effect, skin protection, anti-aging and blood circulation improvement, 0.01 to 0.4 wt % of a *camellia sinensis* leaf extract having functions of providing skin soothing and skin aging prevention, 0.01 to 0.3 wt % of a *glycyrrhiza inflata* root extract having functions of providing skin moisturizing, skin soothing and an anti-inflammatory effect, 0.01 to 0.3 wt % of a *cnidium officinale* root extract having functions of providing skin soothing, skin elasticity improvement and skin regeneration, 0.01 to 0.5 wt % of an *astragalus membranaceus* root extract having functions of providing whitening, skin control and blood circulation improvement, and 0.01 to 0.4 wt % of a *cinnamomum cassia* bark extract having functions of providing an anti-inflammatory effect, an antioxidant effect, skin protection and skin soothing, so that the bubble type waterless shampoo composition is appropriate as an indoor product.

According to the present invention, desirably, the bubble type waterless shampoo composition further includes any one or more of 0.1 to 0.5 wt % of menthol having functions of a denaturizing agent, a sweetening agent and perfume, 0.001 to 0.3 wt % of a *bambusa vulgaris* leaf extract having functions of providing an antioxidant effect, an anti-bacterial effect, an anti-atopic dermatitis effect and a scalp moisturizing effect, 0.01 to 0.4 wt % of a *helianthus annuus* (sunflower) sprout extract having functions of providing an antioxidant effect, supplement of vitamins, supplement of minerals and skin regeneration, and 0.01 to 0.3 wt % of *euterpe oleracea* fruit oil having functions of providing an antioxidant effect, supplement of vitamins and supplement of amino and omega acids, so that the bubble type waterless shampoo composition is appropriate as an outdoor product.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGURE is a photograph showing the states of scalp and hair before and after the treatment with a bubble type waterless shampoo composition according to the present invention.

DETAILED DESCRIPTION OF THE PREFERRED EMBODIMENTS

Hereinafter, an explanation on a bubble type waterless shampoo composition according to the present invention will be in detail given with reference to the attached drawing.

The conventional shampoo gives stimulus to a user having sensitive scalp and has a shape of paste phase, so that water is first applied to hair and the shampoo is then applied to the hair to generate bubbles through massaging and finally cleaned with water. So as to remove the inconveniences caused by the conventional shampoo, a bubble type waterless shampoo composition according to the present invention has appropriate contents of components contained therein to exert a high cleaning force and is very convenient in use, without having any cleaning with water, so that it is very useful to those people such as the aged, long-stay patients and patients on the danger list, the social weak like the disabled, mariners, soldiers, mountain-climbers, travelers in remote places, leisure participants enjoying fishing, camping, cycling, motorcycling and the like, and the people living in the places where water is lacking like a desert area and a cold area.

According to the present invention, a bubble type waterless shampoo composition includes potassium cocoyl hydrolyzed collagen, palmitoyl oligopeptide, cocamidopropyl betaine, a citric acid, sodium carbonate, *origanum vulgare* leaf oil, a gallic acid, glycerin and aqua water.

In more detail, the bubble type waterless shampoo composition includes 0.1 to 5 wt % of the potassium cocoyl hydrolyzed collagen as a natural surfactant having functions of a detergent, a hair conditioner and a skin conditioner.

The bubble type waterless shampoo composition includes 0.01 to 2 wt % of the palmitoyl oligopeptide as a natural surfactant having functions of a detergent and a skin conditioner.

The bubble type waterless shampoo composition includes 0.1 to 7 wt % of the cocamidopropyl betaine as an amphoteric ion having functions of an anti-static agent, a hair conditioner, a scalp conditioner, a detergent, a foaming agent and a water-soluble thickening agent. Through the function of the foaming agent of the cocamidopropyl betaine, the shampoo can be used without water.

The bubble type waterless shampoo composition includes 0.01 to 0.8 wt % of the citric acid as an organic acid having functions of a PH control agent, a metal ion sequestering agent and perfume.

The bubble type waterless shampoo composition includes 0.1 to 4 wt % of the sodium carbonate as inorganic salt having a function of a PH control agent.

The bubble type waterless shampoo composition includes 0.01 to 0.5 wt % of the *origanum vulgare* leaf oil having functions of perfume, an antioxidant and a skin protector.

The bubble type waterless shampoo composition includes 0.01 to 0.6 wt % of the gallic acid having a function of an astringent.

The bubble type waterless shampoo composition includes 0.01 to 3 wt % of the glycerin having functions of a denaturizing agent, perfume, a hair conditioner, a skin moisturizer, a skin protector and a viscosity plasticizer.

The bubble type waterless shampoo composition includes the rest of aqua water having a function of a solvent made by refining tap water through distilling or ion-exchange resin ion.

So as to provide skin stimulus reduction and hair loss prevention, according to the present invention, desirably, the bubble type waterless shampoo composition further includes any one or more of *pisum sativum* (pea) peptide, butylenes glycol, a sigesbeckia orientalis extract, a sapindus mukurossi fruit extract, PEG-120 methyl glucose dioleate and decyl glucoside.

According to the present invention, there is provided 1 to 5 wt % of the *pisum sativum* (pea) peptide that activates stem cells of scalp, gives energy to hair roots and helps hair growth to provide hair loss prevention.

According to the present invention, there is provided 3 to 5 wt % of the butylenes glycol having functions of perfume, a skin conditioner, a solvent, viscosity plasticizer and scalp moisturizer. Through the use of butylenes glycol, at this time, an amount of glycerin used can be reduced to minimize skin stimulus and strengthen skin stability.

According to the present invention, there is provided 0.01 to 0.1 wt % of the sigesbeckia orientalis extract as a natural preservative having a function of preventing the deformation of a product. Through the use of sigesbeckia orientalis extract, at this time, the period for the use of the product can be extended.

According to the present invention, there is provided 0.1 to 5 wt % of the sapindus mukurossi fruit extract as a surfactant having a function of increasing the number of bubbles formed and the duration time of the bubbles.

According to the present invention, there is provided 1 to 5 wt % of the PEG-120 methyl glucose dioleate as a water-soluble thickening agent having functions of reducing the stimulus caused by the surfactant, preventing the reduction of the bubbles of the surfactant and performing scalp moisturizing. In this case, sodium carbonate used for the existing products may be replaced with the PEG-120 methyl glucose dioleate.

According to the present invention, there is provided 5 to 20 wt % of the decyl glucoside as a natural surfactant having a complex sugar component which is extracted from sugar beets, corns, coconuts and palm nugget oil and has a function of biodegradability. In this case, cocoamidopropyl betain used for the existing products may be replaced with the decyl glucoside.

According to the present invention, the bubble type waterless shampoo composition further includes any one or more of saponin, a *camellia sinensis* leaf extract, a *glycyrrhiza inflata* root extract, a *cnidium officinale* root extract, an *astragalus membranaceus* root extract and a *cinnamomum cassia* bark extract, so that the bubble type waterless shampoo composition is appropriate as an indoor product.

According to the present invention, there is provided 0.01 to 0.2 wt % of the saponin having functions of providing an antioxidant effect, skin protection, anti-aging and blood circulation improvement.

According to the present invention, there is provided 0.01 to 0.4 wt % of the *camellia sinensis* leaf extract having functions of providing skin soothing and skin aging prevention.

According to the present invention, there is provided 0.01 to 0.3 wt % of the *glycyrrhiza inflata* root extract having functions of providing skin moisturizing, skin soothing and anti-inflammatory effects.

According to the present invention, there is provided 0.01 to 0.3 wt % of the *cnidium officinale* root extract having functions of providing skin soothing, skin elasticity improvement and skin regeneration.

According to the present invention, there is provided 0.01 to 0.5 wt % of the *astragalus membranaceus* root extract having functions of providing whitening, skin control and blood circulation improvement.

According to the present invention, there is provided 0.01 to 0.4 wt % of the *cinnamomum cassia* bark extract having functions of providing an anti-inflammatory effect, an anti-oxidant effect, skin protection and skin soothing, According to the present invention, the bubble type waterless shampoo composition further includes any one or more of menthol, a *bambusa vulgaris* leaf extract, a *helianthus annuus* (sunflower) sprout extract and *euterpe oleracea* fruit oil, so that the bubble type waterless shampoo composition is appropriate as an outdoor product.

According to the present invention, there is provided 0.1 to 0.5 wt % of the menthol having functions of a denaturizing agent, a sweetening agent and perfume.

According to the present invention, there is provided 0.001 to 0.3 wt % of the *bambusa vulgaris* leaf extract having functions of providing an antioxidant effect, an anti-bacterial effect, an anti-atopic dermatitis effect and a scalp moisturizing effect.

According to the present invention, there is provided 0.01 to 0.4 wt % of the *helianthus annuus* (sunflower) sprout extract having functions of providing an antioxidant effect, supplement of vitamins, supplement of minerals and skin regeneration.

According to the present invention, there is provided 0.01 to 0.3 wt % of the *euterpe oleracea* fruit oil having functions of providing an antioxidant effect, supplement of vitamins and supplement of amino and omega acids.

According to the present invention, the bubble type waterless shampoo composition has a clear liquid having a light yellow color. In case of the indoor product, the bubble type waterless shampoo composition has a natural fragrance generated from the *origanum vulgare* leaf oil, and in case of the outdoor product, it has a natural fragrance generated from the mixture of the *origanum vulgare* leaf oil and the menthol.

According to the bubble type waterless shampoo composition, bubbles are produced by means of pumping and directly sprayed onto a user's scalp, and otherwise, his or her scalp rubs against the bubbles put into his or her hand, thus shampooing his or her scalp and hair.

After the shampooing, no separate cleaning liquid for removing the shampoo composition from the scalp and hair is needed, and accordingly, the shampooed scalp and hair are just cleaned through a dry towel, thus removing impurities like sebum existing on the scalp, foreign substances existing on the scalp and the remaining shampoo composition.

The states of scalp and hair before and after the treatment with the bubble type waterless shampoo composition according to the present invention are photographed using a 400 times microscope, and after a photographing result, as shown in FIGURE, it is found that the scalp and hair are enough cleaned with the bubble type waterless shampoo composition according to the present invention.

As shown in FIGURE, before the shampoo treatment pores are closed with sebum, and the sebum is attached even to scalp and hair. However, after the shampoo treatment the sebum inside the pores and attached to the scalp and hair are completely removed, thus providing high cleaning effects.

On the other hand, the bubble type waterless shampoo composition according to the present invention makes use of natural materials as all of raw materials used for the indoor and outdoor products and does not use any components of ethanol, petroleum, silicone, pigments and sulfate, thus minimizing chemical influences giving the human bodies and improving the stability for living bodies.

Further, all components used in the present invention are only the vegetable oil or extracts extracted from natural plants, thus optimizing an eco-friendly effect, scalp stimulation suppression, scalp stability, scalp protection and scalp regeneration.

As described above, the bubble type waterless shampoo composition according to the present invention can be conveniently used for patients before and after operations, the aged, the disabled, and people during outdoor activities who do not have their scalp care for a long period of time, without having any separate cleaning with water.

Further, the bubble type waterless shampoo composition according to the present invention has natural extracts as effective components thereof to exert a high cleaning force, thus providing skin moisturizing, skin regeneration, itching release and nutrition supplement.

Furthermore, the bubble type waterless shampoo composition according to the present invention can activate stem cells of scalp and minimizing skin stimulus, thus providing hair loss prevention.

Additionally, the bubble type waterless shampoo composition according to the present invention can strengthen skin moisturizing, skin regeneration, and skin and hair conditioning functions if provided as an indoor product.

In addition, the bubble type waterless shampoo composition according to the present invention can provide ultraviolet protection and antioxidant action to protect a user's scalp and hair from strong ultraviolet rays in his or her outdoor activities if provided as an outdoor product.

Further, the bubble type waterless shampoo composition according to the present invention can contain a menthol component to refresh his or her scalp, to release dandruff and itching, and to maintain his or her scalp in a healthy state if provided as an outdoor product.

Furthermore, the bubble type waterless shampoo composition according to the present invention can contain natural components having strong antioxidant action to minimize the oxidation occurring on a user's scalp or hair in his or her outdoor activities if provided as an outdoor product.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A waterless shampoo composition comprising:
   0.1 to 5 wt % of potassium cocoyl hydrolyzed collagen as a natural surfactant having a function of a detergent;
   0.01 to 2 wt % of palmitoyl oligopeptide as a natural surfactant having a function of the detergent;
   0.1 to 7 wt % of cocamidopropyl betaine as an amphoteric ion having functions of an anti-static agent, a hair conditioner, a scalp conditioner, the detergent, a foaming agent and a water-soluble thickening agent;
   0.01 to 0.8 wt % of a citric acid as an organic acid having a function of a PH control agent;
   0.1 to 4 wt % of sodium carbonate as inorganic salt having a function of the PH control agent;
   0.01 to 0.5 wt % of *origanum vulgare* leaf oil having functions of perfume, an antioxidant and a skin protector;
   0.01 to 0.6 wt % of a gallic acid having a function of an astringent;
   0.01 to 3 wt % of glycerin having functions of a denaturizing agent, a perfume, the hair conditioner, a skin moisturizer, a skin protector and a viscosity plasticizer; and
   the rest of aqua water having a function of a solvent made by refining tap water through distilling or ion-exchange resin ion.

2. The waterless shampoo composition according to claim 1, further comprising any one or more of 1 to 5 wt % of *pisum sativum* (pea) peptide having a function of providing hair loss prevention through the activation of stem cells of scalp, 3 to 5 wt % of butylene glycol having functions of providing skin stimulus release and scalp moisturizing, 0.01 to 0.1 wt % of a sigesbeckia orientalis extract as a natural preservative having a function of preventing the deformation of a product, 0.1 to 5 wt % of a sapindus mukurossi fruit extract as a surfactant having a function of increasing the number of bubbles formed and the duration time of the bubbles, 1 to 5 wt % of PEG-120 methyl glucose dioleate as a thickening agent having functions of reducing the stimulus caused by the surfactant, preventing the reduction of the bubbles of the surfactant and performing scalp moisturizing, and 5 to 20 wt % of decyl glucoside as a natural surfactant having a function of biodegradability.

3. The waterless shampoo composition according to claim 1, further comprising any one or more of 0.01 to 0.2 wt % of saponin having functions of providing an antioxidant effect, skin protection, anti-aging and blood circulation improvement, 0.01 to 0.4 wt % of a *camellia sinensis* leaf extract having functions of providing skin soothing and skin aging prevention, 0.01 to 0.3 wt % of a *glycyrrhiza inflata* root extract having functions of providing skin moisturizing, skin soothing and an anti-inflammatory effect, 0.01 to 0.3 wt % of a *cnidium officinale* root extract having functions of providing skin soothing, skin elasticity improvement and skin regeneration, 0.01 to 0.5 wt % of an *astragalus membranaceus* root extract having functions of providing whitening, skin control and blood circulation improvement, and 0.01 to 0.4 wt % of a *cinnamomum cassia* bark extract having functions of providing an anti-inflammatory effect, an antioxidant effect, skin protection and skin soothing.

4. The waterless shampoo composition according to claim 3, further comprising any one or more of 0.1 to 0.5 wt % of menthol having functions of a denaturizing agent, a sweetening agent and perfume, 0.001 to 0.3 wt % of a *bambusa vulgaris* leaf extract having functions of providing an antioxidant effect, an anti-bacterial effect, an anti-atopic dermatitis effect and a scalp moisturizing effect, 0.01 to 0.4 wt % of a *helianthus annuus* (sunflower) sprout extract having functions of providing an antioxidant effect, supplement of vitamins, supplement of minerals and skin regeneration, and 0.01 to 0.3 wt % of *euterpe oleracea* fruit oil having functions of providing an antioxidant effect, supplement of vitamins and supplement of amino and omega acids.

* * * * *